United States Patent [19]

Harris et al.

[11] Patent Number: 5,610,161
[45] Date of Patent: Mar. 11, 1997

[54] THERAPEUTIC AGENTS

[75] Inventors: Paul J. Harris; Frank Kerrigan, both of Nottingham, England

[73] Assignee: The Boots Company PLC, Nottingham, England

[21] Appl. No.: 424,388

[22] PCT Filed: Oct. 23, 1993

[86] PCT No.: PCT/EP93/02951

§ 371 Date: Apr. 28, 1995

§ 102(e) Date: Apr. 28, 1995

[87] PCT Pub. No.: WO94/11346

PCT Pub. Date: May 26, 1994

[30] Foreign Application Priority Data

Nov. 9, 1992 [GB] United Kingdom ............... 9223445

[51] Int. Cl.$^6$ .................... C07D 221/20; A61K 31/445
[52] U.S. Cl. ................................ 514/278; 546/16
[58] Field of Search ................. 546/16; 514/278

[56] References Cited

U.S. PATENT DOCUMENTS

| 4,430,335 | 2/1984 | Stupczewski et al. | 424/267 |
| 4,515,960 | 5/1985 | Teetz | 548/408 |

OTHER PUBLICATIONS

Bogeso, K. P. et al. *J. Med. Chem.* 30, 142–150 (1987).
Sundberg, R. J. et al. *J. Org. Chem.* 53, 976–983 (1988).
The international search report for PCT/EP93/02951.
Kloetzel et al, J.A.C.S. 83 (5), 1128–1132 (17 Mar. 1961).
Pearson et al, J.A.C.S. 114 (4), 1329–1345 (12 Feb. 1992).

*Primary Examiner*—Mukund J. Shah
*Assistant Examiner*—King Lit Wong
*Attorney, Agent, or Firm*—Nikaido, Marmelstein, Murray & Oram LLP

[57] ABSTRACT

Compounds of formula I

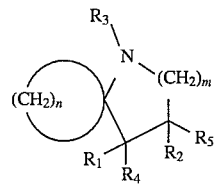

and pharmaceutically acceptable salts thereof in which m is an integer from 1 to 3; n is an integer from 2 to 6; $R_1$ is phenyl optionally substituted by one or more substituents selected from halo, hydroxy, alkoxy, alkanoyl, alkyl, halogenated alkyl, alkylthio, alkylsulphinyl, alkylsulphonyl, cyano, nitro, optionally substituted amino, optionally substituted sulphamoyl, optionally substituted carbamoyl or phenyl, or $R_1$ is naphthyl;

$R_2$ is H, alkyl or phenyl;
$R_3$ is H, alkyl, alkenyl or alkoxyalkyl;
$R_4$ is H or hydroxy; and
$R_5$ is H or together with $R_4$ represents a bond;

have utility in the treatment of obesity and affective disorders such as depression and anxiety.

13 Claims, No Drawings

THERAPEUTIC AGENTS

This is a 371 of PCT/EP93/02951, filed Oct. 23, 1993. The present invention relates to novel therapeutic agents, to processes for their preparation, to pharmaceutical compositions containing them and to their use in the treatment of obesity and affective disorders such as depression and anxiety.

The present invention provides compounds of formula I

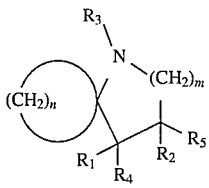

and pharmaceutically acceptable salts thereof
in which m is an integer from 1 to 3;
n is an integer from 2 to 6;

$R_1$ is phenyl optionally substituted by one or more substituents selected from halo, hydroxy, alkoxy containing 1 to 3 carbon atoms, alkanoyl containing 2 or 3 carbon atoms, alkyl containing 1 to 3 carbon atoms, halogenated alkyl containing 1 to 3 carbon atoms, alkylthio containing 1 to 3 carbon atoms, alkylsulphinyl containing 1 to 3 carbon atoms, alkylsulphonyl containing 1 to 3 carbon atoms, cyano, nitro, amino optionally substituted by 1 or 2 alkyl groups each containing 1 to 3 carbon atoms, sulphamoyl optionally substituted by 1 or 2 alkyl groups each containing 1 to 3 carbon atoms, carbamoyl optionally substituted by 1 or 2 alkyl groups each containing 1 to 3 carbon atoms, or phenyl, or $R_1$ is naphthyl;

$R_2$ is H, alkyl containing 1 to 3 carbon atoms or phenyl;

$R_3$ is H, alkyl containing 1 to 6 carbon atoms, alkenyl containing 3 to 6 carbon atoms, or alkoxyalkyl in which the alkoxy group contains 1 to 4 carbon atoms and the alkyl group contains 2 to 4 carbon atoms;

$R_4$ is H or hydroxy; and $R_5$ is H or together with $R_4$ represents a bond.

In preferred compounds of formula I, n is 4 or 5.
In preferred compounds of formula I, m is 1 or 2.
In preferred compounds of formula I, $R_1$ is phenyl optionally substituted by one or more substituents selected from halo (for example fluoro, chloro, bromo or iodo), hydroxy, halogenated alkyl containing 1 to 3 carbon atoms in which halo is fluoro, alkoxy containing 1 or 2 carbon atoms or phenyl or $R_1$ is naphthyl. In more preferred compounds of formula I, $R_1$ is phenyl optionally substituted by one or more substituents selected from chloro, fluoro, hydroxy, trifluoromethyl, methoxy or phenyl or $R_1$ is naphthyl. In especially preferred compounds of formula I, $R_1$ is phenyl, 3-chlorophenyl, 4-chlorophenyl, 3,4-dichlorophenyl, 4-fluorophenyl, 3-(trifluoromethyl)phenyl, 4-hydroxyphenyl, 4-methoxyphenyl, 4-biphenylyl or 2-naphthyl.

In preferred compounds of formula I, $R_2$ is H.

In preferred compounds of formula I, $R_3$ is H, alkyl containing 1 to 3 carbon atoms, alkenyl containing 3 to 6 carbon atoms or alkoxyalkyl in which the alkoxy group contains 1 to 3 carbon atoms and the alkyl group contains 2 or 3 carbon atoms. In more preferred compounds of formula I, $R_3$ is H, methyl, ethyl, propyl, allyl or 2-methoxyethyl. In especially preferred compounds of formula I, $R_3$ is H.

In preferred compounds of formula I, $R_4$ is hydroxy and $R_5$ is H, $R_4$ and $R_5$ are both H, or $R_4$ and $R_5$ together represent a bond. In more preferred compounds of formula I, $R_4$ and $R_5$ together represent a bond.

Compounds of formula I may exist as salts with pharmaceutically acceptable acids. Examples of such salts include hydrochlorides, hydrobromides, sulphates, methanesulphonates, nitrates, maleares, acetates, citrates, fumarates, tartrates [e.g. (+)-tartrates, (−)-tartrates or mixtures thereof including racemic mixtures), succinates, benzoates and salts with amino acids such as glutamic acid. Compounds of formula I and their salts may exist in the form of solvates (for example hydrates).

Certain compounds of formula I may exist in more than one crystal form and the present invention includes each crystal form and the mixtures thereof.

Compounds of formula I which contain one or more chiral centres exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the active moiety is transformed by the separation procedures described above, a further step is required to convert the product to the active moiety. Alternatively, specific enantiomers may be synthesised by asymmetric synthesis using optically active reagents, substrates, catalysts or solvents, or by converting one enantiomer to the other by asymmetric transformation.

Specific compounds of formula I are:
5-(4-chlorophenyl)-1-azaspiro[5.5]undec-4-ene;
5-(3-chlorophenyl)-1-azaspiro[5.5]undec-4-ene;
5-(3,4-dichlorophenyl)-1-azaspiro[5.5]undec-4-ene;
5-(4-fluorophenyl)-1-azaspiro[5.5]undec-4-ene;
5-[3-(trifluoromethyl)phenyl]-1-azaspiro[5.5]undec-4-ene;
5-(2-naphthyl)-1-azaspiro[5.5]undec-4-ene;
5-(4-hydroxyphenyl)-1-azaspiro[5.5]undec-4-ene;
5-(4-chlorophenyl)-1-methyl-1-azaspiro[5.5]undec-4-ene;
10-(4-chlorophenyl)-6-azaspiro[4.5]dec-9-ene;
5-(4-chlorophenyl)-5-hydroxy-1-azaspiro[5.5]-undecane;
5-(4-chlorophenyl)-1-ethyl-5-hydroxy-1-azaspiro[5.5]undecane;
5-(3-chlorophenyl)-5-hydroxy-1-azaspiro[5.5]undecane;
5-(3,4-dichlorophenyl)-5-hydroxy-1-azaspiro[5.5]undecane;
5-(4-chlorophenyl)-1-azaspiro[5.5]undecane;
5-(4-methoxyphenyl)-1-azaspiro[5.5]undecane;
5-(4-chlorophenyl)-1-propyl-1-azaspiro[5.5]undec-4-ene;
1-allyl-5-(4-chlorophenyl)-1-azaspiro[5.5]undec-4-ene;
5-(4-chlorophenyl)-1-(2-methoxyethyl)-1-azaspiro[5.5]undec-4-ene;
5-phenyl-1-azaspiro[5.5]undec-4-ene;
5-(4-biphenylyl)-1-azaspiro[5.5]undec-4-ene;
4-(4-chlorophenyl)-1-azaspiro[4.5]dec-3-ene;
and pharmaceutically acceptable salts thereof.

The present invention also includes pharmaceutical compositions containing a therapeutically effective amount of a compound of formula I together with a pharmaceutically acceptable diluent or carrier.

As used hereinafter, the term "active compound" denotes a compound of formula I. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1 to 500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tabletting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a nontoxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat obesity and affective disorders such as depression and anxiety. Whilst the precise amount of active compound administered in such treatment will depend on a number of factors, for example the age of the patient, the severity of the condition and the past medical history, and always lies within the sound discretion of the administering physician, the amount of active compound administered per day is in the range 1 to 1000 mg preferably 5 to 500 mg given in a single or in divided doses at one or more times during the day.

In yet another aspect, the present invention provides the use of a compound of formula I in the manufacture of a medicament for use in the treatment of obesity and affective disorders such as depression and anxiety.

Processes for the preparation of compounds of formula I will now be described. These processes form a further aspect of the present invention.

Compounds of formula I in which $R_4$ and $R_5$ together represent a bond may be prepared by dehydration of a compound of formula I in which $R_4$ is hydroxy and $R_5$ is H, for example in the presence of (a) sulphuric acid or (b) toluene-4-sulphonic acid and toluene.

Compounds of formula I in which $R_3$ is alkyl, may be prepared by alkylation of a compound of formula I in which $R_3$ is H, for example with an alkyl halide, optionally in the presence of a base, for example potassium carbonate, or by reductive alkylation with an aldehyde or a ketone and formic acid or a reducing agent such as sodium cyanoborohydride, or by acylation of a compound of formula I in which $R_3$ is H with an acylating agent such as an acyl halide, for example, acetyl chloride, or a carboxylic anhydride, for example, acetic anhydride, followed by reaction with a reducing agent, for example, borane-methyl sulphide complex. Compounds of formula I in which $R_3$ is methyl, may be prepared by methylation of a compound of formula I in which $R_3$ is H, for example, using formaldehyde and formic acid.

Compounds of formula I in which $R_3$ is ethyl may be prepared by acylation of a compound of formula I in which $R_3$ is H, for example, using acetic anhydride, followed by reduction with borane-methyl sulphide complex.

Compounds of formula I in which $R_3$ is alkenyl, may be prepared by reaction of a compound of formula I in which $R_3$ is H, for example with an alkenyl halide optionally in the presence of a base, for example potassium carbonate.

Compounds of formula I in which $R_3$ is alkoxyalkyl, may be prepared by reaction of a compound of formula I in which $R_3$ is H, for example with an alkoxyalkyl halide optionally in the presence of a base, for example potassium carbonate.

Compounds of formula I in which $R_4$ and $R_5$ are both H may be prepared by reduction of a compound of formula I in which $R_4$ and $R_5$ together represent a bond with a suitable reducing agent, for example hydrogen in the presence of 10% palladium-on-carbon catalyst, and in a suitable solvent, for example ethanol.

Compounds of formula I in which $R_4$ is hydroxy and $R_5$ is H may be prepared by reaction of a compound of formula II

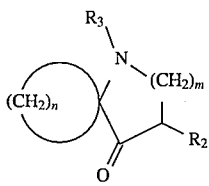

with an organometallic reagent, for example an organolithium compound of formula III

   III or a Grignard reagent of formula IV

   IV in which X is chloro, bromo or iodo, in a suitable solvent system, followed by hydrolytic work-up.

Compounds of formula II may be prepared by reaction of a compound of formula V

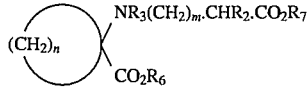

in which $R_6$ and $R_7$ are the same or different and are alkyl groups containing 1 to 4 carbon atoms, with a base, for example sodium alkoxide, to give a compound of formula VI

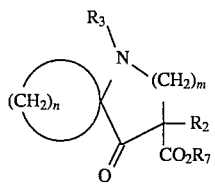

which is then treated with aqueous acid to give a compound of formula II.

Compounds of formula II may be prepared from compounds of formula V, by addition of a base, for example, sodium alkoxide followed by addition of aqueous acid, without the isolation of compounds of formula VI.

Compounds of formula V may be prepared by reaction of a compound of formula VII

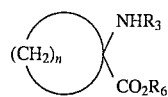

with a compound of formula VIII

in which Z is a leaving group, for example chloro, bromo or iodo in the presence of a base, for example potassium carbonate.

Compounds of formula VII may be prepared by esterification of a compound of formula IX

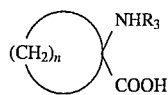

with an alcohol of formula $R_6OH$ optionally in the presence of an acid catalyst.

The therapeutic activity of the compounds of the present invention is illustrated by the following tests performed on standard laboratory animals.

Test 1—mice

The therapeutic activity of the compounds of formula I has been indicated by assessing the ability of the compounds to reverse the hypothermic effects of reserpine in the following manner. Male mice of the Charles River CD1 strain weighing between 18 and 30 g were separated into groups of five and were supplied with food and water ad libitum. After five hours the body temperature of each mouse was taken orally and the mice were injected intraperitoneally with reserpine (10 mg/kg) in solution in deionised water containing ascorbic acid (50 mg/ml). The amount of liquid injected was 10 ml/kg of body weight. Nine hours after the start of the test food was withdrawn but water was still available ad libitum. Twenty-four hours after the start of the test the temperatures of the mice were taken and the mice were given the test compound orally at a dose volume of 10 ml/kg of body weight. The compound was administered in aqueous solution. Three hours later the temperatures of all the mice were again taken. The percentage reversal of the reserpine-induced fall in body temperature was then calculated by the formula:

$$\frac{[(\text{Temp after 27 hrs}) - (\text{Temp after 24 hrs})] \times 100}{(\text{Temp after 5 hrs}) - (\text{Temp after 24 hrs})}$$

The percentage reversal value for each group of five mice was determined at more than one dose rate to enable a value of the dose which causes a 50% reversal ($ED_{50}$) to be obtained. Examples of compounds which gave $ED_{50}$ values of 30 mg/kg or less are given in Table 1. It is widely understood by those skilled in the art that this test is indicative of compounds having antidepressant activity in humans.

Test 2—rats

The therapeutic activity of the compounds of formula I has been indicated by assessing the ability of the compounds to prevent the prosis (eye closure) induced by reserpine in the following manner. Male rats of the Charles River CD strain weighing between 140 and 180 g were randomly separated into five rats in each cage and supplied with food and water ad libitum. Eighteen hours prior to initiation of the test four of the five rats were marked with a pen such that each rat was individually identifiable; food was then withdrawn. The following morning, two hours before the test, the rats were weighed and a semi-randomised code was used to allocate treatments to rats. The test commenced by orally administering either:

a) the test compound in solution in deionised water at a dose volume of 10 ml/kg of body weight, followed by immediate intravenous injection of 1 ml/kg of body weight of reserpine (0.75 mg/kg) in solution in deionised water containing 238 mM citric acid, 1.02% v/v Tween 80 and 0.2% v/v benzyl alcohol (treated group);

b) deionised water at a dose volume of 10 ml/kg of body weight, followed by immediate intravenous injection of 1 ml/kg of body weight of reserpine (0.75 mg/kg) in solution in deionised water containing 238 mM citric acid, 1.02% v/v Tween 80 and 0.2% v/v benzyl alcohol (positive control group); or c) deionised water at a dose volume of 10 ml/kg of body weight, followed by immediate intravenous injection of 1 ml/kg of body weight of deionised water containing 238 mM citric acid, 1.02% v/v Tween 80 and 0.2% v/v benzyl alcohol (negative control group).

Three hours later rats were individually placed in clear perspex boxes (42×22×22 cm) and observed by a person who was unaware of the treatment received by each animal. The degree of prosis was scored 45 seconds and 75 seconds later using the following observer rating system: 0=eye fully open, 1=eye ¼ closed, 2=eye ½ closed, 3=eye ¾ closed, 4=eye fully closed. A mean ptosis score was then calculated for all identically treated rats usually comprising a group of eight rats. The mean prosis score of the negative control group was then subtracted from the mean ptosis score of the positive control group to give the ptosis score induced by reserpine in the absence of the test compound. The mean ptosis score for each group of treated rats was determined at more than one dose of test compound to enable a value for the dose ($ED_{50}$) which causes a 50% prevention of the reserpine-induced ptosis to be obtained. Examples of compounds which gave $ED_{50}$ values of 30 mg/kg or less are given in Table 1. It is widely understood by those skilled in the art that this test is indicative of compounds having antidepressant activity in humans.

TABLE 1

| Example No. | Test 1 $ED_{50}$ (mg/kg) | Test 2 $ED_{50}$ (mg/kg) |
| --- | --- | --- |
| 1 | Inactive @ 30 | 11.3 |
| 2 | ~16 | 8.1 |
| 3 | 10.7 | 7.7 |
| 4 | Inactive @ 30 | 2.2 |
| 5 | ~20 | 7.0 |
| 6 | 14.1 | 2.7 |
| 7, 23 | 2.0 | 1.4 |
| 8 | 16.4 | 5.1 |
| 9 | ~11 | 3.9 |
| 10 | ~18 | 8.5 |
| 11 | ~22 | Inactive @ 30 |
| 12 | 11.9 | 11.9 |
| 13 | Inactive @ 30 | 21.8 |
| 14 | ~12 | 30.0 |
| 15 | 6.9 | 3.8 |
| 16 | 9.4 | 3.3 |
| 17 | ~23 | 3.1 |
| 18 | 4.8 | 0.5 |
| 19 | ~14 | 5.8 |
| 20 | ~26 | 3.0 |
| 21 | Inactive @ 30 | 9.1 |
| 22 | ~30 | 10.1 |

TABLE 1-continued

| Example No. | Test 1 $ED_{50}$ (mg/kg) | Test 2 $ED_{50}$ (mg/kg) |
| --- | --- | --- |
| 24 | ~11.5 | Inactive @ 30 |
| 25 | Inactive @ 30 | 9.9 |
| 26 | Inactive @ 30 | 5.6 |

The invention is illustrated by the following Examples which are given by way of example only. The final products of each of these Examples were characterised by one or more of the following procedures: gas-liquid chromatography, elemental analysis, nuclear magnetic resonance spectroscopy and infra-red spectroscopy.

EXAMPLE A

A mixture of 1-aminocyclohexanecarboxylic acid (62.4 g) and saturated ethanolic hydrogen chloride solution (400 ml) was heated under reflux for 7 hours then allowed to stand at ambient temperature for 2 days. The mixture was resaturated with hydrogen chloride and heated under reflux for a further 23 hours. The solvent was removed in vacuo, and the residue diluted with ice-water and basified by the addition of an excess of 5M aqueous sodium hydroxide solution. The product was extracted into ether, the extracts were washed with water, dried over magnesium sulphate, and the solvent removed in vacuo to give ethyl 1-aminocyclohexanecarboxylate. Yield 50.6 g.

A mixture of ethyl 1-aminocyclohexanecarboxylate (37.1 g, prepared in a similar manner to that described above), potassium carbonate (37 g), and ethyl 4-bromobutyrate (42.3 g) was stirred at 100° C. for 10 hours, cooled to ambient temperature and diluted with ice-water. The product was extracted into ether and the extracts were washed with water, dried over magnesium sulphate, and the solvent removed in vacuo to give an oil (46.6 g). Unreacted ethyl 4-bromobutyrate was removed by distillation (bp 64° C. at 1.6 mbar), and the residual ethyl 1-(3-ethoxycarbonylpropylamino)cyclohexanecarboxylate was used without further purification. Yield 30.5 g.

Sodium (8.9 g) was dissolved in ethanol (175 ml) and the solvent was removed in vacuo. The residue was mixed at ambient temperature with ethyl 1-(3-ethoxycarbonylpropylamino)cyclohexanecarboxylate (55.2 g, prepared in a similar manner to that described above) and the stirred mixture was heated to 145° C. while ethanol formed in the reaction was removed by distillation. When evolution of ethanol ceased, the residue was dissolved in hot propan-2-ol (185 ml). The solution was cooled to ambient temperature, diluted with water and acidified to pH 1 by the addition of concentrated hydrochloric acid. The solution was then basified by the addition of an excess of solid potassium carbonate and the product was extracted into ethyl acetate. The extracts were dried over magnesium sulphate and the solvent removed in vacuo to yield ethyl 5-oxo-1-azaspiro[5.5]undecane-4-carboxylate. Yield 30.6 g.

A mixture of ethyl 5-oxo-1-azaspiro[5.5]undecane-4-carboxylate (13.9 g, prepared in a similar manner to that described above), concentrated hydrochloric acid (50 ml) and water (50 ml) was heated at 90°–95° C. for 5 hours. The solvent was removed in vacuo, and the residue diluted with ice-water (50 ml) and basified by the addition of an excess of 5M aqueous sodium hydroxide solution. The product was extracted into ethyl acetate and the extracts were washed with brine, dried over magnesium sulphate, and the solvent removed in vacuo to give 1-azaspiro[5.5]undecan-5-one as a pale brown solid. Yield 5.9 g, mp 55° C.

EXAMPLE B

Sodium (9.4 g) was dissolved in ethanol (185 ml) and the solvent removed in vacuo. The residue was mixed at ambient temperature with ethyl 1-(3-ethoxycarbonylpropylamino)cyclohexanecarboxylate (52.7 g, prepared in a similar manner to that described in Example A) and the stirred mixture was heated to 160° C. while ethanol formed in the reaction was removed by distillation. When evolution of ethanol ceased, the last traces of solvent were removed in vacuo to yield a solid which was cooled to ambient temperature, dissolved in a mixture of water (200 ml) and propan-2-ol (300 ml) and allowed to stand at ambient temperature for 48 hours. The solution was cooled in ice and acidified to pH 1 by the addition of concentrated hydrochloric acid. The mixture was then basified by the addition of an excess of solid potassium carbonate and allowed to stand at ambient temperature for 24 hours. The product was extracted into ethyl acetate, the extracts dried over magnesium sulphate and the solvent removed in vacuo to yield 1-azaspiro[5.5]undecan-5-one as a pale brown solid. Yield 20.5 g, mp 55° C.

was extracted into ethyl acetate and the extracts were washed with water, dried over magnesium sulphate and the solvent removed in vacuo.

The crude products were purified by procedures identified in the column headed "Nb" to give compounds of structure I in which $R_4$ is hydroxy and $R_5$ is H (h g).

Notes to Table 2

In the column headed mp(°C.), the letters "ND" indicate that the melting point was not determined.

2.1 The crude product was triturated with petroleum ether (bp 40°–60° C.) to yield the free base as a solid.

2.2 The crude product was triturated with ethyl acetate to yield the free base as a solid.

2.3 Low-boiling impurities were removed by distillation in vacuo at 100° C. at 0.6 mbar to leave a brown oil. The oil was triturated with ethyl acetate to yield the free base as a solid.

2.4 The crude product was triturated with ethyl acetate to yield a solid which was purified further via preparative scale high performance liquid chromatography over silica using methanol as eluent. Appropriate fractions were combined and the solvent removed in vacuo to yield the free base as a solid.

TABLE 2

| Ex No | $R_1$ | a | b | c | d | e | f | f" | g | h | Nb | mp (°C.) |
|---|---|---|---|---|---|---|---|---|---|---|---|---|
| C | 4-Chlorophenyl | 39.7 | 263 (k) | 4.98 | 0.5 | 14.31 | 97 | 0 | 24 | 9.62 | 2.1 | 143–145 |
| D | 3-Chlorophenyl | 14.2 | 75 (k) | 1.78 | 0.5 | 5.0 | 340 | 100 | 2.5 | 4.28 | 2.2 | 128–130 |
| E | 3,4-Dichlorophenyl | 36.4 | 180 (l) | 3.9 | 1.5 | 8.6 | 0 | 80 | 48 | 3.55 | 2.2 | ND |
| F | 4-Fluorophenyl | 6.37 | 35 (l) | 0.9 | 2.5 | 2.5 | 0 | 20 | 24 | 1.00 | 2.2 | 170–171.5 |
| G | 3-(Trifluoromethyl)-phenyl | 19.35 | 100 (k) | 2.1 | 1.0 | 6.0 | 20 | 60 | 24 | 3.15 | 2.2 | ND |
| H | 4-Methoxyphenyl | 60.36 | 170 (k) 100 (l) | 3.8 | 0.5 | 10.0 | 0 | 100 | 24 | 3.89 | 2.3 | ND |
| I | 2-Naphthyl | 27.8 | 100 (k) 100 (l) | 2.3 | 1.0 | 6.6 | 0 | 70 | 24 | 2.20 | 2.4 | ND |

EXAMPLE C to I

A compound of formula $R_1MgBr$ in which $R_1$ is as defined in Table 2 was prepared under nitrogen by the dropwise addition of a solution of a compound of formula $R_1Br$ (a g) in a solvent (b ml) which was ether (k) or tetrahydrofuran (l) or a mixture thereof to magnesium metal (c g) initially at ambient temperature, then, when the exothermic reaction commenced, at reflux temperature. After the addition was complete, the mixture was stirred at ambient temperature for d hours.

A solution of 1-azaspiro[5.5]undecan-5-one (e g) in a solvent which was ether (f ml), tetrahydrofuran (f" ml) or a mixture thereof was then added dropwise at 0° C. to the stirred solution of $R_1MgBr$. The mixture was stirred for g hours at ambient temperature in Examples C to G and under reflux in Examples H and I. The reaction mixture (cooled if necessary) was then quenched by cautious addition to a saturated aqueous ammonium chloride solution. The product

EXAMPLE J

4-Chlorophenylmagnesium bromide was prepared under nitrogen by the dropwise addition of a solution of 4-bromochlorobenzene (20.35 g) in ether (160 ml) to magnesium metal (2.6 g) initially at ambient temperature, then, when the exothermic reaction commenced, at reflux temperature. After the addition was complete, the mixture was stirred at ambient temperature for 1 hour.

The stirred solution was then heated to reflux temperature and a solution of 1-azaspiro[5.5]undecan-5-one (9.7 g, prepared as described in Example A) in toluene (160 ml) was added dropwise whilst the ether was removed by distillation until the internal temperature rose to approximately 95° C. The mixture was then heated under reflux for 2 hours, allowed to cool to ambient temperature, and then quenched by addition to an excess of saturated aqueous ammonium chloride solution. The product was extracted into ethyl acetate (3×300 ml) and the extracts were combined and dried over magnesium sulphate. The solvent was removed in vacuo and the residue triturated with ethyl acetate. The resulting solid was collected by filtration, washed with ethyl acetate, and dried in vacuo at ambient temperature to give 5-(4-chlorophenyl)-5-hydroxy-1-azaspiro[5.5]undecane as a white solid. Yield 6.7 g, mp 158°–164° C.

Examples 1 to 3

The compounds of formula I prepared in Examples C to E were converted into their hydrochloride salts by saturating ethereal solutions of the compounds with hydrogen chloride. The melting points of the resulting hydrochloride salts are given in Table 3.

TABLE 3

| Ex No. | Starting Material | mp (°C.) |
| --- | --- | --- |
| 1 | C | >250 (dec) |
| 2 | D | 294–295 (dec) |
| 3 | E | 307 (dec) |

Example 4

A mixture of 5-(4-chlorophenyl)-5-hydroxy-1-azaspiro[5.5]undecane (3 g, prepared as described in Example C) and acetic anhydride (45 ml) was heated at 90°–95° C. for 16 hours. The excess of acetic anhydride was removed in vacuo and the residue triturated with ether to yield a solid which was collected by filtration. The filtrate was allowed to stand at ambient temperature for 1 hour, facilitating the precipitation of further solid, which was collected by filtration.

A mixture of the combined solids (2.3 g) and tetrahydrofuran (21 ml) was heated to reflux temperature under nitrogen and borane-methyl sulphide complex (2.3 g) was added dropwise over 35 minutes whilst dimethyl sulphide was removed by distillation. After the addition was complete, the mixture was heated under reflux for 4.5 hours then the solvent was removed in vacuo and the residue was heated to 100° C. 5M hydrochloric acid (1.5 ml) and water (12.4 ml) were added and the solution was heated at 100° C. for 45 minutes. The mixture was then cooled to ambient temperature and 5M aqueous sodium hydroxide solution (2.3 ml) was added.

The solution was then saturated with solid potassium carbonate and the product was extracted into ether. The extracts were washed with water, dried over magnesium sulphate and the solvent was removed in vacuo to yield an oil (1.7 g). The oil was combined with further oil (0.4 g, prepared in a similar manner) of similar purity, and purified by flash chromatography over silica using a 9:1 mixture of dichloromethane and ethyl acetate as eluent. Appropriate fractions were combined, the solvents removed in vacuo, and the resulting oil (1.9 g) was distilled to give an oil. Yield 1.3 g, bp 150°–155° C. at 0.4–0.5 mbar.

The oil (1.3 g) was dissolved in ether (20 ml) and the solution saturated with hydrogen chloride. The solvent was removed in vacuo and the residue was triturated with a mixture of dichloromethane and ether. The resulting solid was collected by filtration and dried in vacuo at ambient temperature to give 5-(4-chlorophenyl)-1-ethyl-5-hydroxy-1-azaspiro[5.5]undecane hydrochloride as an off-white solid. Yield 0.6 g, mp 146°–148° C.

Example 5

5-(4-Chlorophenyl)-5-hydroxy-1-azaspiro[5.5]undecane (5.9 g, prepared as described in Example C) was dissolved in concentrated sulphuric acid (75 ml) and stirred at ambient temperature for 3 hours. The mixture was then poured slowly into ice-water (300 ml) and the resulting solid collected by filtration, washed with a little water and dried in vacuo at ambient temperature over phosphorus pentoxide to give 5-(4-chlorophenyl)-1-azaspiro[5.5]undec-4-ene sulphate as a white solid. Yield 6.2 g, mp 228°–233° C.

Example 6

A mixture of 5-(4-chlorophenyl)-1-azaspiro[5.5]undec-4-ene sulphate (0.5 g, prepared as described in Example 5) and water (5 ml) was stirred at ambient temperature to give, initially, a mobile suspension which rapidly thickened. Water (5 ml) was added to aid mobility and the solid was collected by filtration, washed with water (5 ml) and dried in vacuo at ambient temperature to give 5-(4-chlorophenyl)-1-azaspiro[5.5]undec-4-ene 0.5 sulphate, 2.1 hydrate as a white solid. Yield 0.3 g, mp 205°–215° C.

Example 7

A suspension of 5-(4-chlorophenyl)-1-azaspiro[5.5]undec-4-ene sulphate (13 g prepared in a similar manner to that described in Example 5) in 1M aqueous sodium hydroxide solution (200 ml) was stirred at ambient temperature for 1 hour, then the free base was extracted into ether (3×150 ml). The extracts were combined, dried over magnesium sulphate, concentrated to a volume of 150 ml, and filtered. The filtrate was cooled in ice and saturated with hydrogen chloride. The resulting solid was collected by filtration, washed with ether, and dried in vacuo at ambient temperature for 24 hours and at 60° C. for 8 hours to give 5-(4-chlorophenyl)-1-azaspiro[5.5]undec-4-ene hydrochloride as a white solid. Yield 8.6 g, mp >300° C.

Example 8

5-(3-Chlorophenyl)-5-hydroxy-1-azaspiro[5.5]undecane (2.5 g, prepared as described in Example D) was dissolved in concentrated sulphuric acid (35 ml) and stirred at ambient temperature for 2 hours. The mixture was then poured cautiously onto ice (100 ml) and the resulting white precipitate was collected by filtration and suspended in ethyl acetate (300 ml). 5M Aqueous sodium hydroxide solution (250 ml) was added and the mixture was stirred at ambient temperature for 15 minutes. The aqueous layer was separated and extracted with ethyl acetate (2×200 ml), then the combined organic solutions were washed with water, dried over magnesium sulphate and the solvent removed in vacuo. The resulting oil was dissolved in ether (100 ml), charcoal (1 g) was added, and the mixture was heated under reflux for 5 minutes and hot-filtered. The cooled filtrate was saturated with hydrogen chloride and the resulting solid collected, washed with ether and dried in vacuo at ambient temperature to give 5-(3-chlorophenyl)-1-azaspiro[5.5]undec-4-ene hydrochloride as a white solid. Yield 2.1 g, mp 281°–282° C. (dec).

Example 9

5-(3,4-Dichlorophenyl-5-hydroxy-1-azaspiro[5.5]undecane (3.0 g, prepared as described in Example E) was dissolved in concentrated sulphuric acid (35 ml) and stirred at ambient temperature for 4 hours, then the mixture was poured cautiously onto ice (100 ml). The resulting white precipitate was collected by filtration and suspended in 5M aqueous sodium hydroxide solution (200 ml). The mixture was stirred at ambient temperature for 15 minutes, then the product was extracted into ether (2×250 ml). The combined extracts were washed with water, dried over magnesium sulphate and filtered. The filtrate was cooled in ice, saturated with hydrogen chloride and the resulting solid collected by filtration, washed with ether and dried in vacuo at ambient temperature to give 5-(3,4-dichlorophenyl)-1-azaspiro[5.5] undec-4-ene hydrochloride as a white solid. Yield 2.5 g, mp 332° C. (dec).

Example 10

5-(4-Fluorophenyl)-5-hydroxy-1-azaspiro[5.5]undecane (1.27 g, prepared in a similar manner to that described in Example F) was dissolved in concentrated sulphuric acid (25 ml) and stirred at ambient temperature for 2 hours, then the solution was carefully poured onto ice (50 ml), and the sticky solid collected by filtration. The solid was triturated with ether (2×50 ml), collected by filtration, washed with ether and dried in vacuo at ambient temperature to give a solid which was triturated with hot ether (70 ml), collected by filtration washed with ether and dried in vacuo at 60° C. to give 5-(4-fluorophenyl)-1-azaspiro[5.5]undec-4-ene sulphate as a white solid. Yield 1.3 g, mp 195°–200° C.

Example 11

5-Hydroxy-5-[3-(trifluoromethyl)phenyl]-1-azaspiro[5.5] undecane (2.2 g, prepared as described in Example G) was dissolved in concentrated sulphuric acid (25 ml) and stirred at ambient temperature for 4 hours. The mixture was poured cautiously onto ice (100 ml) and the resulting white precipitate was collected by filtration, and suspended in 5M aqueous sodium hydroxide solution (250 ml). The mixture was stirred at ambient temperature for 15 minutes then the product was extracted into ethyl acetate (2×125 ml). The combined extracts were washed with water, dried over magnesium sulphate and the solvent removed in vacuo. The resulting oil was dissolved in ether and the solution was filtered. The filtrate was cooled in ice, saturated with hydrogen chloride and the resulting solid collected by filtration, washed with ether and dried in vacuo at ambient temperature to give 5-[3-(trifluoromethyl)phenyl]-1-azaspiro[5.5]undec-4-ene hydrochloride as a white solid. Yield 1.0 g, mp >250° C. (sublimes).

Example 12

A mixture of 5-hydroxy-5-(2-naphthyl)-1-azaspiro[5.5] undecane (2.1 g, prepared as described in Example I), p-toluenesulphonic acid (1.62 g) and toluene (500 ml) was heated under reflux for 20 hours while water evolved in the reaction was removed by azeotropic distillation (Dean-Stark apparatus). More toluene (500 ml) and p-toluenesulphonic acid (2.4 g) were added, and heating under reflux continued for a further 35 hours. The cooled mixture was poured into 5M aqueous sodium hydroxide solution (500 ml) and stirred vigorously for 5 minutes. Ethyl acetate (250 ml) was added and stirring continued for 5 minutes. The aqueous layer was separated and further extracted with ethyl acetate (2×500 ml). The organic solutions were combined, washed with water, dried over magnesium sulphate and the solvents removed in vacuo to give an oil. The oil was purified by flash-chromatography over silica using toluene/triethylamine (95:5) as the eluent. Appropriate fractions were combined and the solvents removed in vacuo. The resulting oil was dissolved in ether, the solution was filtered, and the filtrate cooled in ice and saturated with hydrogen chloride. The resulting solid was collected by filtration, washed with ether and dried in vacuo at ambient temperature to give 5-(2-naphthyl)-1-azaspiro[5.5]undec-4-ene hydrochloride as a white solid. Yield 1.8 g, mp 297°–302° C.

Example 13

A mixture of 5-hydroxy-5-(4-methoxyphenyl)-1-azaspiro [5.5]undecane (2.8 g, prepared as described in Example H), p-toluenesulphonic acid (2.3 g) and toluene (150 ml) was heated under reflux for 17 hours while water evolved in the reaction was removed by azeotropic distillation (Dean-Stark apparatus). The cooled mixture was poured onto 5M aqueous sodium hydroxide solution (500 ml) and stirred vigorously for 5 minutes. Ethyl acetate (250 ml) was added and stirring continued for 5 minutes. The aqueous layer was separated and further extracted with ethyl acetate (2×500 ml). The organic solutions were combined, washed with water, dried over magnesium sulphate and the solvents removed in vacuo to give an oil. The oil was dissolved in ether, the solution filtered, and the filtrate cooled in ice and saturated with hydrogen chloride. The resulting solid was collected by filtration, washed with ether and dried in vacuo at ambient temperature to give 5-(4-methoxyphenyl)-1-azaspiro[5.5]undec-4-ene hydrochloride as a white solid. Yield 2.7 g, mp 257°–266° C. (dec).

A mixture of 5-(4-methoxyphenyl)-1-azaspiro[5.5]undec-4-ene hydrochloride (1.0 g), glacial acetic acid (20 ml) and hydrobromic acid (48%, 20 ml) was heated under reflux for 6.5 hours then allowed to cool. The mixture was neutralised by the addition of saturated aqueous sodium hydrogen carbonate solution and the product extracted into ether (3×100 ml). The extracts were combined, dried over magnesium sulphate and the solvent removed in vacuo to give a solid which was purified via flash chromatography over silica using toluene/triethylamine (4:1) as eluent. Appropriate fractions were combined, the solvents were removed in vacuo, and the resulting product was dissolved in ether. The solution was filtered, and the filtrate cooled in ice and saturated with hydrogen chloride. The resulting solid was collected by filtration, washed with ether and dried in vacuo at ambient temperature to give 5-(4-hydroxyphenyl)-1-azaspiro[5.5]undec-4-ene hydrochloride as a white solid. Yield 0.7 g, mp 285°–295° C.

Example 14

5-(4-Chlorophenyl)-5-hydroxy-1-azaspiro[5.5]undecane (5.1 g, prepared in a similar manner to that described in Example C) was dissolved in concentrated sulphuric acid (70 ml) and stirred at ambient temperature for 4 hours. The mixture was poured onto ice (300 ml) and the resulting solid was collected by filtration, suspended in water (150 ml) and basified by addition of 5M aqueous sodium hydroxide solution. The resulting solid, 5-(4-chlorophenyl)-1-azaspiro [5.5]undec-4-ene, was collected by filtration and dried in vacuo at ambient temperature.

A mixture of the solid (4.5 g) and ethyl formate (300 ml) was heated under reflux for 48 hours. The mixture was concentrated in vacuo to a small volume and the resulting solid collected by filtration and crystallised from ethyl acetate (60 ml) (the hot solution was decolourised by addition of charcoal) to give 5-(4-chlorophenyl)-1-azaspiro

[5.5]undec-4-ene formate as a white solid. Yield 1.7 g, mp 136°–140° C.

A mixture of 5-(4-chlorophenyl)-1-azaspiro[5.5]undec-4-ene formate (1.7 g), formic acid (15 ml) and 37–40% aqueous formaldehyde solution (30 ml) was heated at approximately 95° C. for 7.5 hours, then cooled in ice. The mixture was basified by the addition of 5M aqueous sodium hydroxide solution, and the product extracted into ethyl acetate (2×150 ml). The extracts were combined, dried over magnesium sulphate and the solvent removed in vacuo to leave an oil which solidified slowly at ambient temperature. The solid was triturated with ether and the mixture filtered. The filtrate was evaporated to leave an oily residue which was dissolved in ether, dried over magnesium sulphate and the solvent removed in vacuo to leave an oil which solidified slowly at ambient temperature. Yield 1.3 g.

The solid was dissolved in ether (80 ml), the solution was filtered, and the filtrate cooled in ice and saturated with hydrogen chloride. The resulting solid was collected by filtration, washed with ether and dried in vacuo at 70° C. to give 5-(4-chlorophenyl)-1-methyl-1-azaspiro[5.5]undec-4-ene hydrochloride as a white solid. Yield 1.2 g, mp 243°–248° C. (dec).

Example 15

A solution of fumaric acid (0.4 g) in methanol (35 ml) was added to a solution of 5-(4-chlorophenyl)-1-azaspiro[5.5]undec-4-ene (1.0 g, prepared in a similar manner to that described in Example 14) in ether (25 ml). The solvents were removed in vacuo and the residue was triturated with ether to yield a white solid, which was collected by filtration and dried in vacuo at ambient temperature to give 5-(4-chlorophenyl)-1-azaspiro[5.5]undec-4-ene fumarate as a white solid. Yield 1.1 g, mp 175°–180.5° C. (dec).

Example 16

A solution of methanesulphonic acid (0.3 g) in ether (15 ml) was added dropwise to a cooled solution of 5-(4-chlorophenyl)-1-azaspiro[5.5]undec-4-ene (0.8 g, prepared in a similar manner to that described in Example 14) in ether (25 ml). The resulting solid was collected by filtration, washed with ether and dried in vacuo at ambient temperature to yield 5-(4-chlorophenyl)-1-azaspiro[5.5]undec-4-ene methanesulphonate as a white solid. Yield 1.0 g, mp 226°–231.5° C.

Example 17

A mixture of 1-aminocyclopentanecarboxylic acid (50.0 g) and saturated ethanolic hydrogen chloride solution (350 ml) was heated under reflux for 6 hours. The mixture was cooled, the solvent was removed in vacuo and the residue diluted with water (150 ml). The resulting solution was basified by the addition of an excess of 5M aqueous sodium hydroxide solution and the product was extracted into ether. The extracts were dried over magnesium sulphate and the solvent removed in vacuo to give ethyl 1-aminocyclopentanecarboxylate. Yield 19.6 g.

The aqueous phase was acidified by the addition of 5M hydrochloric acid and the solvent removed in vacuo. The solid residue was mixed with saturated ethanolic hydrogen chloride solution (230 ml) and the mixture was heated under reflux for 6 hours. The mixture was cooled, the solvent was removed in vacuo and the residue diluted with cold water (100 ml). The mixture was basified by the addition of 5M aqueous sodium hydroxide solution and the product was extracted into ether. The extracts were washed with water, dried over magnesium sulphate and the solvent removed in vacuo to give further ethyl 1-aminocyclopentanecarboxylate. Yield 24.3 g.

A mixture of ethyl 1-aminocyclopentanecarboxylate (43.9 g), potassium carbonate (47.8 g) and ethyl 4-bromobutyrate (54.5 g) was stirred at 100° C. for 10 hours, cooled to ambient temperature and diluted with ice-water. The product was extracted into ether and the extracts were washed with water, dried over magnesium sulphate and the solvent removed in vacuo to give an oil (61.1 g) which was distilled to give ethyl 1-(3-ethoxycarbonylpropylamino)cyclopentanecarboxylate as a colourless oil. Yield 49.5 g, bp 109°–124° C. at 0.6 mbar.

Sodium (8.4 g) was dissolved in ethanol (170 ml) and the solvent was removed in vacuo. The residue was mixed at ambient temperature with ethyl 1-(3-ethoxycarbonylpropylamino)cyclopentanecarboxylate (49.5 g) and the stirred mixture was heated to 100° C. while ethanol formed in the reaction was removed by distillation. When evolution of ethanol ceased, the residue was dissolved in hot propan-2-ol (150 ml). The solution was cooled to ambient temperature, diluted with water and acidified to pH 1 by the addition of concentrated hydrochloric acid. The solution was then basified by the addition of an excess of solid potassium carbonate and the product was extracted into ethyl acetate. The extracts were dried over magnesium sulphate and the solvent removed in vacuo to give ethyl 10-oxo-6-azaspiro[4.5]decan-9-carboxylate. Yield 7.6 g.

A mixture of ethyl 10-oxo-6-azaspiro[4.5]decan-9-carboxylate (7.6 g), concentrated hydrochloric acid (35 ml) and water (35 ml) was heated at 90°–95° C. for 8 hours. The solvent was removed in vacuo and the residue diluted with ice-water (35 ml) and basified by the addition of an excess of 5M aqueous sodium hydroxide solution. The product was extracted into ethyl acetate and the extracts were washed with brine, dried over magnesium sulphate and the solvent removed in vacuo to give 6-azaspiro[4.5]decan-10-one. Yield 3.1 g.

4-Chlorophenylmagnesium bromide was prepared under nitrogen by the dropwise addition of a solution of 4-bromochlorobenzene (9.6 g) in ether (55 ml) to magnesium metal (1.2 g) initially at ambient temperature then, when the exothermic reaction commenced, at reflux temperature. After the addition was complete the mixture was stirred at ambient temperature for 30 minutes. A solution of 6-azaspiro[4.5]decan-10-one (3.1 g, prepared as described above) in ether (25 ml) was added dropwise at 0° C., and the mixture was stirred for 24 hours at ambient temperature. The reaction was quenched by the slow addition of an excess of saturated aqueous ammonium chloride solution, and the resulting solid collected by filtration. The solid was suspended in water and basified by the addition of an excess of 5M aqueous sodium hydroxide solution. The product was extracted into ethyl acetate (3×100 ml), the extracts were dried over magnesium sulphate and the solvent removed in vacuo to give 10-(4-chlorophenyl)-10-hydroxy-6-azaspiro[4.5]decane as an off-white solid. Yield 1.6 g, mp 152°–155° C.

10-(4-Chlorophenyl)-10-hydroxy-6-azaspiro[4.5]decane (1.6 g) was dissolved in concentrated sulphuric acid (18 ml) and stirred at ambient temperature for 1.5 hours. The mixture was poured cautiously onto ice-water (35 ml), stirred at 0° C. for 1 hour and allowed to stand at 4° C. for 24 hours. The product was collected by filtration, washed with water and dried in vacuo at ambient temperature to give 10-(4-chlorophenyl)-6-azaspiro[4.5]dec-9-ene sulphate as an off-white solid. Yield 1.7 g, mp 184°–190° C.

Example 18

A mixture of 5-(4-chlorophenyl)-1-azaspiro[5.5]undec-4-ene (2.8 g, obtained by basification of the hydrochloride salt prepared as described in Example 7), 10% platinum-on-carbon catalyst (0.24 g), ethanol (50 ml) and 2.5M hydrochloric acid (10 ml) was hydrogenated at 1 atmosphere and ambient temperature until hydrogen uptake ceased (2.5 hours), then the mixture was filtered to remove spent catalyst and the solvents were removed in vacuo.

The residue was dissolved in ethanol (80 ml) and the solution was added to fresh 10% platinum-on-carbon catalyst (0.23 g). The mixture was hydrogenated at 1 atmosphere and ambient temperature for 4 hours, then spent catalyst was removed by filtration, and the solvent was removed in vacuo. The residue was purified via reduced pressure flash chromatography over silica, using a 9:1 mixture of toluene and triethylamine containing a trace of ethanol as eluent. Appropriate fractions were combined and the solvents removed in vacuo to leave a solid (2.3 g). The solid was suspended in propan-2-ol (25 ml) and the mixture was heated under reflux, filtered while hot, and allowed to cool. The resulting solid was collected by filtration and dried in vacuo to give a white solid (0.24 g). Concentration of the liquor yielded a second crop of white solid (0.46 g).

The solids were combined, dissolved in ether (35 ml) and the solution was saturated with hydrogen chloride. The resulting solid was collected by filtration and dried in vacuo at 95° C. to give 5-(4-chlorophenyl)-1-azaspiro[5.5]undecane hydrochloride as a white solid. Yield 0.6 g, mp 311°–312° C. (softens 299° C.).

Example 19

A mixture of 5-(4-methoxyphenyl)-1-azaspiro[5.5]undec-4-ene hydrochloride, (0.6 g, prepared as described in Example 13), 10% palladium-on-carbon catalyst (0.18 g), ethanol (40 ml) and water (20 ml) was hydrogenated at 1 atmosphere and ambient temperature until hydrogen uptake ceased. The mixture was filtered to removed spent catalyst, then the solvents were removed in vacuo to leave a white solid (0.6 g). The solid was triturated with ether (25 ml), collected by filtration and dried in vacuo to give 5-(4-methoxyphenyl)-1-azaspiro[5.5]undecane hydrochloride as a white solid. Yield 0.5 g, mp 287°–289° C. (shrinks 285° C.).

Example 20

A mixture of 5-(4-chlorophenyl)-1-azaspiro[5.5]undec-4-ene hydrochloride (2.0 g, prepared as described in Example 7), 1-bromopropane (1 ml), potassium carbonate (2.0 g) and dimethylformamide (10 ml) was stirred at ambient temperature for 24 hours, and at 95° C. for 24 hours. More bromopropane (1 ml) and a catalytic amount of potassium iodide (10 mg) were added and stirring at 95° C. continued for a further 24 hours. More bromopropane (1 ml) was added, and stirring at 95° C. continued for a further 24 hours.

The mixture was cooled to ambient temperature, diluted with 1M aqueous sodium hydroxide solution (100 ml), and the product extracted into ethyl acetate (3×50 ml). The extracts were combined, washed with water (2×30 ml), dried over magnesium sulphate, and the solvent removed in vacuo to leave a brown oil. The oil was dissolved in ether (50 ml) and the solution saturated with hydrogen chloride. The resulting solid was collected by filtration, washed with ether, and dried in vacuo at ambient temperature to give 5-(4-chlorophenyl)-1-propyl-1-azaspiro[5.5]undec-4-ene hydrochloride as an off-white solid. Yield 1.9 g, mp 245°–246° C., (shrinks 230° C.).

Example 21

A mixture of 5-(4-chlorophenyl)-1-azaspiro[5.5]undec-4-ene hydrochloride (2.0 g, prepared as described in Example 7), potassium carbonate (2.0 g), allyl bromide (2.9 ml) and dimethylformamide (25 ml) was stirred at 95° C. for 17 hours, then allowed to cool to ambient temperature. The mixture was diluted with water (60 ml) and basified by the addition of 5M aqueous sodium hydroxide solution (50 ml), then the product was extracted into ethyl acetate (3×100 ml). The extracts were combined, dried over magnesium sulphate, and the solvent removed in vacuo to leave a brown oil which was purified via flash chromatography over silica using a 99:1 mixture of dichloromethane and industrial methylated spirit as eluent. Appropriate fractions were combined and the solvents removed in vacuo to leave a yellow oil (1.4 g) which was dissolved in ether (50 ml). The solution was filtered and added to an ice-cold solution of maleic acid (0.53 g) in ether (150 ml). The resulting solid was collected by filtration, washed with ether, and dried in vacuo at 50° C. to give 1-allyl-5-(4-chlorophenyl)-1-azaspiro[5.5]undec-4-ene maleate as a white solid. Yield 1.2 g, mp 130°–133° C. (shrinks 125° C.).

Example 22

A mixture of 5-(4-chlorophenyl)-1-azaspiro[5.5]undec-4-ene (1.5 g, obtained by basification of the hydrochloride salt prepared as described in example 7), potassium carbonate (1.6 g), 2-methoxyethyl bromide (2.7 ml), and dimethyl formamide (28 ml) was stirred at 95° C. for 67 hours and allowed to cool to ambient temperature. The mixture was diluted with 1M aqueous sodium hydroxide solution (150 ml), and the product extracted into ethyl acetate (3×150 ml). The extracts were combined, washed with water (2×100 ml), dried over magnesium sulphate and the solvent removed in vacuo to leave a yellow oil (1.6 g). The oil was combined with another sample (0.2 g, prepared in a similar manner) and purified via flash chromatography over silica using a 95:5 mixture of toluene and triethylamine as eluent. Appropriate fractions were combined and the solvents removed in vacuo to leave an oil which was dissolved in ether (50 ml). The solution was cooled in ice and saturated with hydrogen chloride. The resulting solid was collected by filtration, washed with ether and dried in vacuo at 50° C. for 7 hours to give 5-(4-chlorophenyl)-1-(2-methoxyethyl)-1-azaspiro[5.5]undec-4-ene 1.25 hydrochloride as a white solid. Yield 0.7 g, mp 135° C. (dec) (softens 95°–100° C.).

Example 23

Ethanol (4 l) was saturated at 0°–5° C. over 4 hours with hydrogen chloride. 1-Aminocyclohexanecarboxylic acid (600 g) was added in one portion and the mixture was stirred and heated under reflux for 8 hours, then allowed to stand at ambient temperature for 72 hours. The solvent was removed in vacuo and the residue was dissolved in ice-water (1 l) and basified to pH 8–9 at 0°–5° C. by the addition of 2M aqueous sodium hydroxide solution. The product was extracted into dichloromethane (4×300 ml) and the extracts were combined and dried over sodium sulphate. The aqueous residues were basified to pH 10 by the addition of more 2M aqueous sodium hydroxide solution and further product was extracted into dichloromethane (4×200 ml). The extracts were combined and dried over sodium sulphate. The dried dichloromethane extracts were combined and the solvent was removed in vacuo to leave ethyl 1-aminocyclohexanecarboxylate as a pale yellow oil. Yield 669 g.

A mixture of ethyl 1-aminocyclohexanecarboxylate (669 g), potassium carbonate (683.1 g) and ethyl 4-bromobutyrate (558 ml) was stirred at 130° C. for 18 hours, then cooled to ambient temperature and poured onto ice-water (3 l). The product was extracted into dichloromethane and the combined extracts were dried over sodium sulphate and the solvent was removed in vacuo to yield ethyl 1-(3-ethoxycarbonylpropylamino)cyclohexanecarboxylate as a brown/orange oil. Yield 943.2 g.

Sodium (8.92 g) was dissolved in ethanol (150 ml) and the solvent was removed in vacuo. Ethyl 1-(3-ethoxycarbonylpropylamino)cyclohexanecarboxylate (50 g) was added and the mixture was stirred at 140° C. while ethanol formed in the reaction was removed by distillation. When evolution of ethanol ceased the mixture was allowed to cool to ambient temperature to yield an orange foam. A solution of concentrated hydrochloric acid (150 ml) in water (150 ml) was added and the mixture was heated at 95° C. for 7 hours. Charcoal was added and the mixture was filtered (hot) through "celite", cooled to ambient temperature, washed with ethyl acetate (2×150 ml), and basified below 20° C. by the addition of 5M aqueous sodium hydroxide solution. The product was extracted into dichloromethane (5×250 ml) and the combined extracts were washed with water (200 ml), dried over sodium sulphate and the solvent removed in vacuo to yield 1-azaspiro[5.5]undecan-5-one as a beige solid. Yield (18.6 g).

The reaction was repeated twice more on the following scale:

sodium (159.3 g)

ethanol (1500 ml)

ethyl 1-(3-ethoxycarbonylpropylamino)cyclohexanecarboxylate (447 g);

Then concentrated hydrochloric acid (1000 ml)

water (1000 ml).

Overall combined yield 245.11 g.

A solution of 1-azaspiro[5.5]undecan-5-one (132.5 g) in toluene (1900 ml) was added under nitrogen over 45 minutes to stirred 4-chlorophenylmagnesium bromide (1M solution in ether; 1904 ml) while the ether solvent was removed by distillation at a rate equivalent to the addition of the toluene solution. After the addition was complete the mixture was stirred at 95° C. for a further 3 hours, cooled to 20° C. and quenched by the dropwise addition of saturated aqueous ammonium chloride solution (1 l). The mixture was filtered through "celite" and the filter bed washed with water and ethyl acetate. The filtrate was separated and the aqueous layer extracted with ethyl acetate. The combined organic solutions were washed with water (500 ml) and the product was extracted into 5M hydrochloric acid (4×250 ml). This caused some hydrochloride salt of the product to precipitate; the solid was collected by filtration and washed with ethyl acetate. The filtrate was separated, and the aqueous layer was washed with ethyl acetate, combined with the solid hydrochloride salt and basified by the addition of 5M aqueous sodium hydroxide solution. The product was extracted into dichloromethane and the combined extracts were washed with water, dried over sodium sulphate and the solvent removed in vacuo to yield a pale yellow solid (136.6 g). The solid was triturated with petroleum ether (bp 40°–60° C.) (500 ml) to give a solid which was collected by filtration and dried in vacuo to give 5-(4-chlorophenyl)-5-hydroxy-1-azaspiro[5.5]undecane as a pale cream solid. Yield 105.2 g.

The reaction was repeated using:

4-Chlorophenylmagnesiumbromide (1M solution in ether, 1618 ml)

1-azaspiro[5.5]undecan-5-one (112.6 g)

Toluene (1.6 l)

Aqueous ammonium chloride solution (1 l).

although the work-up was different: after quenching with ammonium chloride solution, the mixture was filtered through "celite" and the layers separated. The aqueous layer was twice further extracted with ethyl acetate and the combined organic solutions were dried over sodium sulphate and the solvents removed in vacuo to leave an oil. The "celite" filter cake was boiled with ethyl acetate and the mixture was hot filtered through "celite". The filtrate was combined with the oil and the solvent was removed in vacuo. The residue was triturated with ice-cold petroleum ether (bp 60°–80° C.) (1000 ml) to give a solid which was collected by filtration and dried in vacuo to give 5-(4-chlorophenyl)-5-hydroxy-1-azaspiro[5.5]undecane as a beige solid. Yield 129.5 g.

5-(4-Chlorophenyl)-5-hydroxy-1-azaspiro[5.5]undecane (105.1 g) was added in portions to vigorously stirred concentrated sulphuric acid (600 ml) over 20 minutes, then the mixture was stirred at ambient temperature for a further 1 hour and poured carefully onto ice (2 l) causing a white solid to precipitate. The mixture was cooled in ice for 2 hours and the solid was collected by filtration. The solid was basified by addition to an excess of 5M aqueous sodium hydroxide solution and the product was extracted into ether (4×200 ml) followed by dichloromethane (2×250 ml). The extracts were combined, dried over sodium sulphate and the solvents removed in vacuo to give 5-(4-chlorophenyl)-1-azaspiro[5.5]undec-4-ene as a cream solid. Yield 98 g.

The reaction was repeated using 5-(4-chlorophenyl)-5-hydroxy-1-azaspiro[5.5]undecane (129.5 g) and concentrated sulphuric acid (600 ml). Yield 122.5 g.

5M Hydrochloric acid (200 ml) was added slowly to a solution of 5-(4-chlorophenyl)-1-azaspiro[5.5]undec-4-ene (98 g) in ether (1 l) and the mixture was stirred at ambient temperature for 30 minutes. The resulting solid was collected by filtration and washed with cold water followed by dichloromethane to give an off-white solid. The process was repeated using the remainder of 5-(4-chlorophenyl)-1-azaspiro[5.5]undec-4-ene to give further off-white solid. The combined solids were stirred in dichloromethane (1 l) for 1 hour, collected by filtration, washed with dichloromethane (200 ml) and dried in vacuo to give 5-(4-chlorophenyl)-1-azaspiro[5.5]undec-4-ene hydrochloride as an off-white solid. Yield 224.3 g, mp >300° C.

Example 24

A solution of 2-bromochlorobenzene (36.7 ml) in ether (260 ml) was added dropwise under nitrogen to magnesium metal (3.8 g) initially at ambient temperature, then, when the exothermic reaction commenced, at reflux temperature. After the addition was complete the mixture was stirred at ambient temperature for 1 hour. A solution of 1-azaspiro[5.5]undecan-5-one (12.5 g, prepared as described in Example B) in tetrahydrofuran (200 ml) was added at ambient temperature, then the mixture was stirred and heated under reflux for 18 hours. The mixture was cooled to ambient temperature and quenched by addition to an excess of saturated aqueous ammonium chloride solution, then the product was extracted into ethyl acetate (2×300 ml). The extracts were combined, dried over magnesium sulphate and the solvents removed in vacuo to leave a brown oil (46.7 g). Low-boiling impurities were removed by distillation at <100° C. at ~13.3 mbar. The residue, a viscous, brown oil, was triturated in ethyl acetate to give a pale grey solid which was collected by filtration and dried at atmospheric pressure. Yield 0.17 g. The filtrate was allowed to concentrate at atmospheric pressure to give two further crops of pale grey solid (0.11 g+0.47 g). The three crops of solid were combined to give 5-hydroxy-5-phenyl-1-azaspiro[5.5]undecane as a pale grey solid. Yield 0.75 g.

A stirred mixture of 5-hydroxy-5-phenyl-1-azaspiro[5.5]undecane (0.75 g), p-toluenesulphonic acid (1.1 g), and toluene (340 ml) was heated under reflux for 96 hours while water formed in the reaction was removed by azeotropic distillation. Further p-toluenesulphonic acid (2.2 g) was added and heating under reflux was continued for a further 144 hours. The mixture was allowed to cool to ambient temperature and was quenched by addition to an excess of 5M aqueous sodium hydroxide solution. The product was extracted into toluene and the extracts combined, dried over magnesium sulphate and the solvent removed in vacuo to leave an oil (1 g).

The oil was purified via flash chromatography over silica using a 95:5 mixture of toluene and triethylamine as eluent. Appropriate fractions were combined and the solvents removed in vacuo to leave an oil (0.34 g). The oil was dissolved in ether and the solution saturated with hydrogen chloride to give a solid which was collected by filtration, washed with ether, and dried in vacuo to give 5-phenyl-1-azaspiro[5.5]undec-4-ene hydrochloride as a white solid. Yield 0.36 g, mp 268°–275° C.(dec).

Example 25

Approximately one quarter of a solution of 4-bromobiphenyl (7.2 g) in ether (80 ml) was added under nitrogen to magnesium metal (0.75 g). A few drops of iodomethane were added and, when the exothermic reaction commenced, the mixture was stirred and allowed to reach reflux temperature. The remainder of the 4-bromobiphenyl solution was added dropwise at reflux temperature, then the mixture was stirred at reflux temperature for 0.5 hour and the solvent was removed by distillation at atmospheric pressure. A solution of 1-azaspiro[5.5]undecan-5-one (2.1 g, prepared as described in Example B), in toluene (120 ml) was added dropwise at ambient temperature and the mixture was stirred at 95° C. for 18 hours. The mixture was quenched by addition to an excess of saturated aqueous ammonium chloride solution (300 ml) and the product was extracted into ether (3×300 ml+1×400 ml). The extracts were combined and dried over magnesium sulphate and the solvents removed in vacuo to leave a brown semisolid (6.74 g). The semisolid was triturated with ethyl acetate to give a solid which was collected by filtration and dried in vacuo to give 5-(4-biphenylyl)-5-hydroxy-1-azaspiro[5.5]undecane as an off-white solid. Yield 1.3 g.

A stirred mixture of 5-(4-biphenylyl)-5-hydroxy-1-azaspiro[5.5]undecane (1.3 g), toluene (200 ml) and p-toluenesulphonic acid (0.9 g) was heated under reflux for 38.5 hours while water formed in the reaction was removed by azeotropic distillation. Further p-toluenesulphonic acid (0.9 g) was added and heating under reflux was continued for a further 18 hours. Further p-toluenesulphonic acid (1.8 g) was added and heating under reflux continued for 72 hours. The mixture was basified by addition to 5M aqueous sodium hydroxide solution (500 ml) and the product was extracted into ether (200 ml+300 ml). The extracts were combined, dried over magnesium sulphate and the solvents removed in vacuo to leave a pale brown gum (1.15 g).

The product was dissolved in a 1:1 mixture of ether and ethyl acetate (150 ml) and the solution was cooled in ice and saturated with hydrogen chloride. The resulting solid was collected by filtration and dried in vacuo at ambient temperature for 16 hours and at 85° C. for 8 hours to give 5-(4-biphenylyl)-1-azaspiro[5.5]undec-4-ene hydrochloride as a pale brown solid. Yield 0.9 g, mp 288°–292° C.(dec) (shrinks 280° C.).

Example 26

A mixture of ethyl 1-aminocyclohexanecarboxylate (58 g, prepared as described in Example A), potassium carbonate (59 g) and ethyl 3-bromopropionate (61.4 g) was stirred at 110°–135° C. for 32.5 hours, at 120°–145° C. for 3.5 hours, and at 145°–150° C. for a further 3 hours, then poured onto ice-water (600 ml). The product was extracted into ether (2×400 ml) and the extracts were combined, dried over magnesium sulphate and the solvent was removed in vacuo to leave a yellow oil (63.75 g). The oil was distilled to give ethyl 1-(2-ethoxycarbonylethylamino)cyclohexanecarboxylate as a colourless oil. Yield 26.3 g, bp 126°–135° C. at 0.95 mbar.

Sodium (5.0 g) was dissolved in ethanol (280 ml) and the solvent was removed in vacuo. The residue was mixed with ethyl 1-(2-ethoxycarbonylethylamino)cyclohexanecarboxylate (26.3 g), and the stirred mixture was heated to 120° C. while ethanol formed in the reaction was removed by distillation. When evolution of ethanol ceased the mixture was allowed to cool slightly and water (100 ml) and concentrated hydrochloric acid (50 ml) were added. The mixture was heated at 95° C. for 41 hours, then cooled to ambient temperature and basilled by the addition of 5M aqueous sodium hydroxide solution. The product was extracted into ether (3×400 ml) and the extracts were combined, dried over magnesium sulphate and the solvent removed in vacuo to leave 1-azaspiro[4.5]decan-4-one as a brown oil. Yield 12.8 g.

4-Chlorophenylmagnesium bromide was prepared under nitrogen by the dropwise addition of a solution of 4-bromochlorobenzene (27 g) in ether (220 ml) to magnesium metal (3.4 g) initially at ambient temperature, then when the exothermic reaction commenced, at reflux temperature. After the addition was complete the mixture was stirred at reflux temperature for 1.5 hours. A solution of 1-azaspiro[4.5]decan-4-one (9 g) in toluene (220 ml) was added dropwise while the ether solvent was removed by distillation. When the addition was complete, the mixture was stirred at 100°–110° C. for 45 minutes, then allowed to stand at ambient temperature for 16 hours. The mixture was heated for a further 2 hours at 140° C., then cooled to ambient temperature and quenched by addition to saturated aqueous ammonium chloride solution (500 ml). The product was extracted into ethyl acetate (2×300 ml; 1×200 ml) and the extracts were combined, dried over magnesium sulphate and the solvent removed in vacuo to leave an orange/brown semisolid (11.0 g).

The semisolid was triturated with ethyl acetate and the resulting solid was collected by filtration and dried in vacuo at 50° C. to give 4-(4-chlorophenyl)-4-hydroxy-1-azaspiro[4.5]decane as a white solid (2.4 g), containing an impurity identified as 4-hydroxy-1-azaspiro[4.5]decan-1,3-diene. This crude product was used in the next stage without purification.

The crude 4-(4-chlorophenyl)-4-hydroxy-1azaspiro[4.5]decane (2.2 g) was dissolved in concentrated sulphuric acid (27 ml) and the solution was stirred at ambient temperature for 1 hour. The mixture was poured onto ice to give a white precipitate which was collected by filtration, dissolved in water, and basified by the addition of 5M aqueous sodium hydroxide solution. The product was extracted into ether (3×200 ml) and the extracts were combined, dried over magnesium sulphate, and concentrated in vacuo to 100 ml. The solution was saturated with hydrogen chloride and the resulting solid was collected by filtration and dried in vacuo at 60° C. for 7 hours to give 4-(4-chlorophenyl)-1-azaspiro[4.5]dec-3-ene hydrochloride as a white solid. Yield 1.1 g, mp 225°–233° C.(dec).

Example 27

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. Compounds of formula I

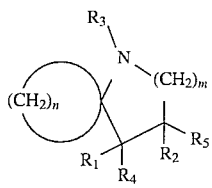

and pharmaceutically acceptable salts thereof
in which m is an integer from 1 to 3;
n is an integer from 2 to 6;
$R_1$ is phenyl optionally substituted by one or more substituents selected from halo, hydroxy, alkoxy containing 1 to 3 carbon atoms, alkanoyl containing 2 or 3 carbon atoms, alkyl containing 1 to 3 carbon atoms, halogenated alkyl containing 1 to 3 carbon atoms, alkylthio containing 1 to 3 carbon atoms, alkylsulphinyl containing 1 to 3 carbon atoms, alkylsulphonyl containing 1 to 3 carbon atoms, cyano, nitro, amino optionally substituted by 1 or 2 alkyl groups each containing 1 to 3 carbon atoms, sulphamoyl optionally substituted by 1 or 2 alkyl groups each containing 1 to 3 carbon atoms, carbamoyl optionally substituted by 1 or 2 alkyl groups each containing 1 to 3 carbon atoms, or phenyl, or $R_1$ is naphthyl;

$R_2$ is H, alkyl containing 1 to 3 carbon atoms or phenyl;

$R_3$ is H, alkyl containing 1 to 6 carbon atoms, alkenyl containing 3 to 6 carbon atoms, or alkoxyalkyl in which the alkoxy group contains 1 to 4 carbon atoms and the alkyl group contains 2 to 4 carbon atoms;

$R_4$ is H or hydroxy; and $R_5$ is H or together with $R_4$ represents a bond.

2. Compounds of formula I as claimed in claim 1 wherein $R_1$ is phenyl optionally substituted by one or more substituents selected from halo, hydroxy, halogenated alkyl containing 1 to 3 carbon atoms in which halo is fluoro, alkoxy containing 1 or 2 carbon atoms or phenyl or $R_1$ is naphthyl.

3. Compounds of formula I as claimed in claim 1 wherein $R_1$ is phenyl optionally substituted by one or more substituents selected from chloro, fluoro, hydroxy, trifluoromethyl, methoxy or phenyl or $R_1$ is naphthyl.

4. Compounds of formula I as claimed in claim 1 wherein $R_1$ is phenyl, 3-chlorophenyl, 4-chlorophenyl, 3,4-dichlorophenyl, 4-fluorophenyl, 3-(trifluoromethyl)phenyl, 4-hydroxyphenyl, 4-methoxyphenyl, 4-biphenylyl or 2-naphthyl.

5. Compounds of formula I as claimed in claim 1 wherein $R_2$ is H.

6. Compounds of formula I as claimed in claim 1 wherein $R_3$ is H, alkyl containing 1 to 3 carbon atoms, alkenyl containing 3 to 6 carbon atoms or alkoxyalkyl in which the alkoxy group contains 1 to 3 carbon atoms and the alkyl group contains 2 or 3 carbon atoms.

7. Compounds of formula I as claimed in claim 1 wherein $R_3$ is H, methyl, ethyl, propyl, allyl or 2-methoxyethyl.

8. Compounds of formula I as claimed in claim 1 wherein $R_3$ is H.

9. Compounds of formula I as claimed in claim 1 wherein $R_4$ is hydroxy and $R_5$ is H, $R_4$ and $R_5$ are both H, or $R_4$ and $R_5$ together represent a bond.

10. Compounds of formula I as claimed in claim 1 wherein $R_4$ and $R_5$ together represent a bond.

11. Compounds of formula I as claimed in claim 1 which are:
5-(4-chlorophenyl)-1-azaspiro[5.5]undec-4-ene;

5-(3-chlorophenyl)-1-azaspiro[5.5]undec-4-ene;
5-(3,4-dichlorophenyl)-1-azaspiro[5.5]undec-4-ene;
5-(4-fluorophenyl)-1-azaspiro[5.5]undec-4-ene;
5-[3-(trifluoromethyl)phenyl]-1-azaspiro[5.5]undec-4-ene;
5-(2-naphthyl)-1-azaspiro[5.5]undec-4-ene;
5-(4-hydroxyphenyl)-1-azaspiro[5.5]undec-4-ene;
5-(4-chlorophenyl)-1-methyl-1-azaspiro[5.5]undec-4-ene;
10-(4-chlorophenyl)-6-azaspiro[4.5]dec-9-ene;
5-(4-chlorophenyl)-5-hydroxy-1-azaspiro[5.5]undecane;
5-(4-chlorophenyl)-1-ethyl -5-hydroxy-1-azaspiro[5.5]undecane;
5-(3-chlorophenyl)-5-hydroxy-1-azaspiro[5.5]undecane;
5-(3,4-dichlorophenyl)-5-hydroxy-1-azaspiro[5.5]undecane;
5-(4-chlorophenyl)-1-azaspiro[5.5]undecane;
5-(4-methoxyphenyl)-1-azaspiro[5.5]undecane;
5-(4-chlorophenyl)-1-propyl-1-azaspiro[5.5]undec-4-ene;
1-allyl-5-(4-chlorophenyl)-1-azaspiro[5.5]undec-4-ene;
5-(4-chlorophenyl)-1-(2-methoxyethyl)-1-azaspiro[5.5]undec-4-ene;
5-phenyl-1-azaspiro[5.5]undec-4-ene;
5-(4-biphenylyl)-1-azaspiro[5.5]undec-4-ene;
4-(4-chlorophenyl)-1-azaspiro[4.5]dec-3-ene;
and pharmaceutically acceptable salts thereof.

12. A method of treating obesity which comprises the administration of a therapeutically effective amount of a compound of formula I as claimed in claim 1 to a patient in need thereof.

13. Pharmaceutical compositions comprising a therapeutically effective amount of a compound of formula I, together with a pharmaceutically acceptable diluent or carrier.

* * * * *

UNITED STATES PATENT AND TRADEMARK OFFICE
CERTIFICATE OF CORRECTION

PATENT NO. : 5,610,161
DATED : March 11, 1997
INVENTOR(S) : Harris et al.

It is certified that error appears in the above-indentified patent and that said Letters Patent is hereby corrected as shown below:

In claim 1, column 24, line 12, delete "integer from 1 to 3;" and insert -- 2; --

Signed and Sealed this

Fifteenth Day of July, 1997

Attest:

BRUCE LEHMAN

Attesting Officer   Commissioner of Patents and Trademarks